US011299762B2

(12) United States Patent
Kasas et al.

(10) Patent No.: US 11,299,762 B2
(45) Date of Patent: Apr. 12, 2022

(54) NANOSCALE MOTION DETECTOR

(71) Applicant: Ecole Polytechnique Fédérale de Lausanne (EPFL), Lausanne (CH)

(72) Inventors: Sandor Kasas, Pully (CH); Giovanni Longo, Lausanne (CH); Giovanni Dietler, Echandens-Denges (CH); Livan Bladimir Alonso Sarduy, Lausanne (CH)

(73) Assignee: ECOLE POLYTECHNIQUE FEDERALE DE, Lausanne (CH)

( * ) Notice: Subject to any disclaimer, the term of this patent is extended or adjusted under 35 U.S.C. 154(b) by 432 days.

(21) Appl. No.: 15/957,694

(22) Filed: Apr. 19, 2018

(65) Prior Publication Data

US 2018/0312898 A1    Nov. 1, 2018

Related U.S. Application Data

(62) Division of application No. 14/350,451, filed as application No. PCT/IB2012/055564 on Oct. 12, 2012, now abandoned.

(30) Foreign Application Priority Data

Oct. 14, 2011    (WO) ................... PCT/IB2011/054553

(51) Int. Cl.
*G01N 33/543*    (2006.01)
*C12Q 1/18*    (2006.01)
(Continued)

(52) U.S. Cl.
CPC .................. *C12Q 1/18* (2013.01); *C12Q 1/02* (2013.01); *C12Q 1/533* (2013.01); *G01N 29/022* (2013.01); *G01N 29/036* (2013.01); *G01N 29/2418* (2013.01); *G01N 29/46* (2013.01); *G01N 33/54366* (2013.01); *B82Y 5/00* (2013.01); *B82Y 35/00* (2013.01); *G01N 2291/0427* (2013.01)

(58) Field of Classification Search
CPC . C12Q 1/18; C12Q 1/02; C12Q 1/533; G01N 29/022; G01N 29/036; G01N 29/2418; G01N 29/46; G01N 33/54366; G01N 2291/0427; B82Y 5/00; B82Y 35/00; B81B 2203/0118
USPC ............ 73/862.634, 862, 639; 310/311, 340; 435/6.15, 288.7; 436/518, 524
See application file for complete search history.

(56) References Cited

U.S. PATENT DOCUMENTS 7,148,017 B1 * 12/2006 Craighead ............ G01N 29/022 435/7.1
2006/0121502 A1 * 6/2006 Cain ................ G01N 33/54373 435/6.19

(Continued)

FOREIGN PATENT DOCUMENTS

JP    2006-337249 A    12/2006
JP    2007-3234 A    1/2007

OTHER PUBLICATIONS

Bosco, IEEE, 2011, pp. 877-880 (Year: 2011).*

*Primary Examiner* — Christopher L Chin
(74) *Attorney, Agent, or Firm* — Sughrue Mion, PLLC

(57) ABSTRACT

Motion detector comprising a flexible support (1,5) adapted to hold at least one object (6-9), a sensor (4) for measuring the displacement of said support (1) and processing means for differentiating the fluctuations of said support (1) from those induced by said object (6-9).

12 Claims, 10 Drawing Sheets

(51) Int. Cl.
    *G01N 29/036*     (2006.01)
    *G01N 29/24*     (2006.01)
    *G01N 29/46*     (2006.01)
    *G01N 29/02*     (2006.01)
    *C12Q 1/02*     (2006.01)
    *C12Q 1/533*     (2006.01)
    *B82Y 5/00*     (2011.01)
    *B82Y 35/00*     (2011.01)

(56) References Cited

U.S. PATENT DOCUMENTS

2006/0191320 A1     8/2006   Pinnaduwage et al.
2008/0261297 A1   10/2008   Chaffey et al.

\* cited by examiner

NANOSCALE MOTION DETECTOR

This application is a division of U.S. patent application Ser. No. 14/350,451 filed Apr. 8, 2014; which is the U.S. national phase of International Application No. PCT/162012/055564 filed Oct. 12, 2012, which designated the U.S. and claims priority to PCT/IB2011/054553 filed Oct. 14, 2011, the entire contents of each of which are hereby incorporated by reference.

FIELD OF INVENTION

The present invention relates to the analysis at a very low scale of objects having a size ranging from Angstroms to micrometers. It particularly but not exclusively relates to the detection of the movement or the inner dynamics of said objects.

STATE OF THE ART

In recent years, micro and nano mechanical oscillators have become a new class of sensors, and very delicate oscillators, coupled with sensitive displacement detectors, have resulted in a number of extraordinarily powerful experimental techniques (1). Remarkably, up to now, the application of such devices has been mostly limited to measurements of resonance frequency to determine the presence of very small masses (2-7) or to the static determination of the stress deflections induced by the presence of specific nanosized systems (8-13).

Moreover, the sensitivity of most of the techniques described in literature is greatly reduced in presence of liquid environments (14).

To summarize, the use of those state of the art sensors is limited to a static type determination of very small objects.

Providing a precise and efficient dynamic type measurement of very small objects would be of great interest for a large community.

GENERAL DESCRIPTION OF THE INVENTION

The present invention concerns a motion detector as defined in the claims.

The detector comprises a flexible support adapted to hold at least one object (for instance an object having a movement or an intrinsic dynamics), a sensor for measuring the displacement said support and processing means for differentiating the movement of said support from the one induced by the said object.

The invention also concerns a method for analysing small sized specimens, ranging typically front Angstroms to micrometers.

The method according to the invention can be used in any of environment, vacuum, air, liquid or physiological medium.

In the present text the term "fluctuation" encompasses any type of motion, in particular the vibration and the deflection.

The invention may be particularly useful for detecting the movement or intrinsic dynamics (or absence of them) of biological objects such as proteins, lipids, nucleic acids, glucides, viruses, bacteria or cells in presence or absence of external or internal stimuli. In the present text, the terms "object" and "objects" are to be interpreted as being limited to "biological objects" as herein defined.

It may also be used for analysing objects which may show an activity which induces a displacement of the flexible support. The induced displacement of the said support may occur by the movement of the object, by the thermal fluctuations induced by the object, by changes in the interaction between the object and the flexible support, by the internal dynamics of the object or by any physical, chemical or biological phenomenon generated by the object and provoking the fluctuations of the said support.

DETAILED DESCRIPTION OF THE INVENTION

The invention will be better understood in the present chapter, with a detailed description including some non-limiting examples illustrated by the following figures.

NUMERICAL REFERENCES USED IN THE FIGURES

Figure 1:
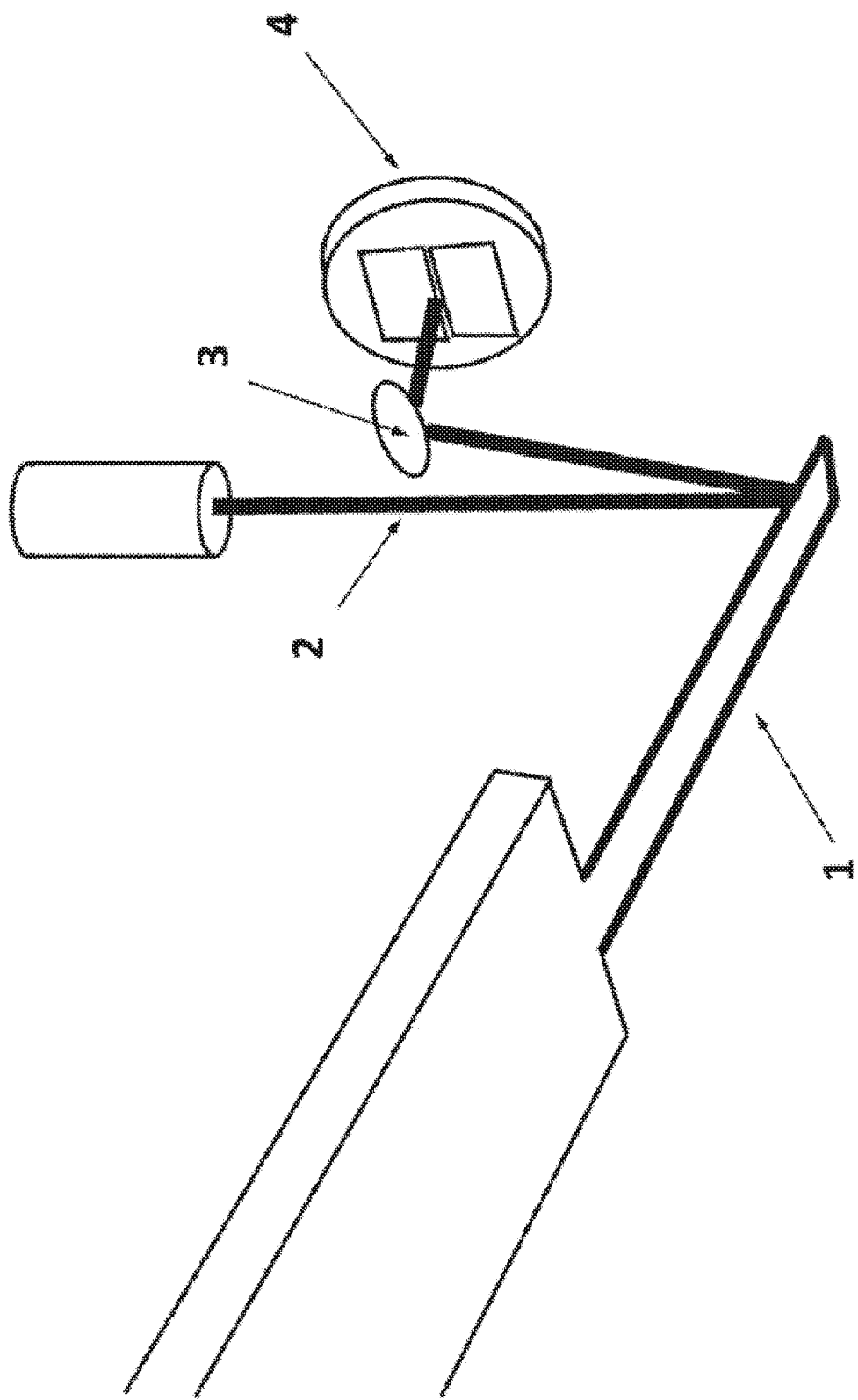
FIG. 1 illustrates a first setup according to the invention for sensing movement at the nanoscale.

1. Cantilever
2. Laser beam
3. Mirror
4. Photodetector
5. Optical fibre
6. Moving specimen
7. TopoII
8. DNA molecule
9. Bacteria FIG. 1 represents a first embodiment of the invention with a motion detector comprising a cantilever 1, a laser beam 2, a mirror 3 and two or four segments photodiodes 4.

Figure 2:
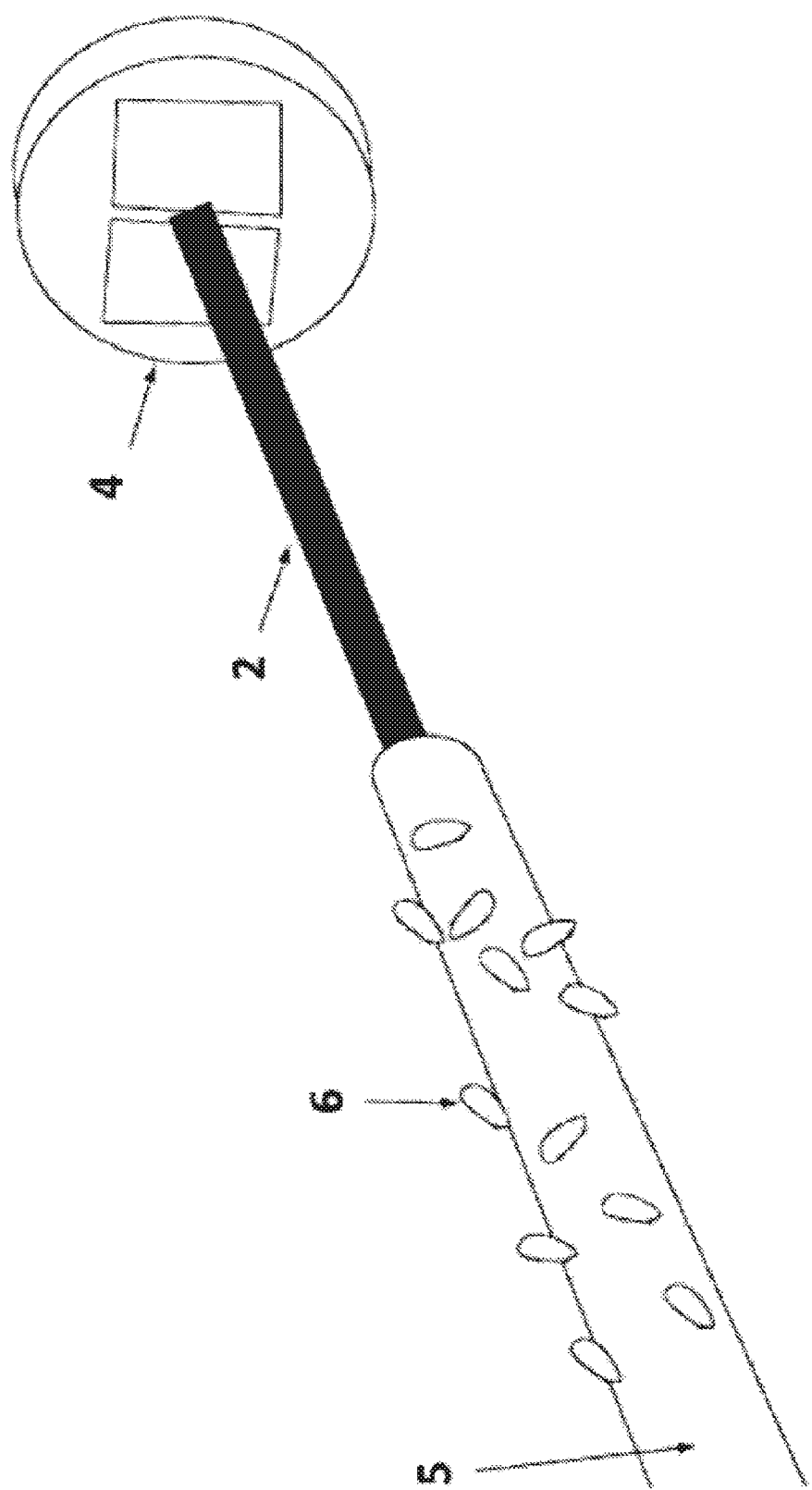
FIG. 2 illustrates another setup according to the invention for sensing movement at the nanoscale.

FIG. 2 represents a similar assembly but where the cantilever is replaced by an optical fibre 5 and where the laser beam 2 is collimated in the fibre 5 and is collected towards its free end.

Figure 3:
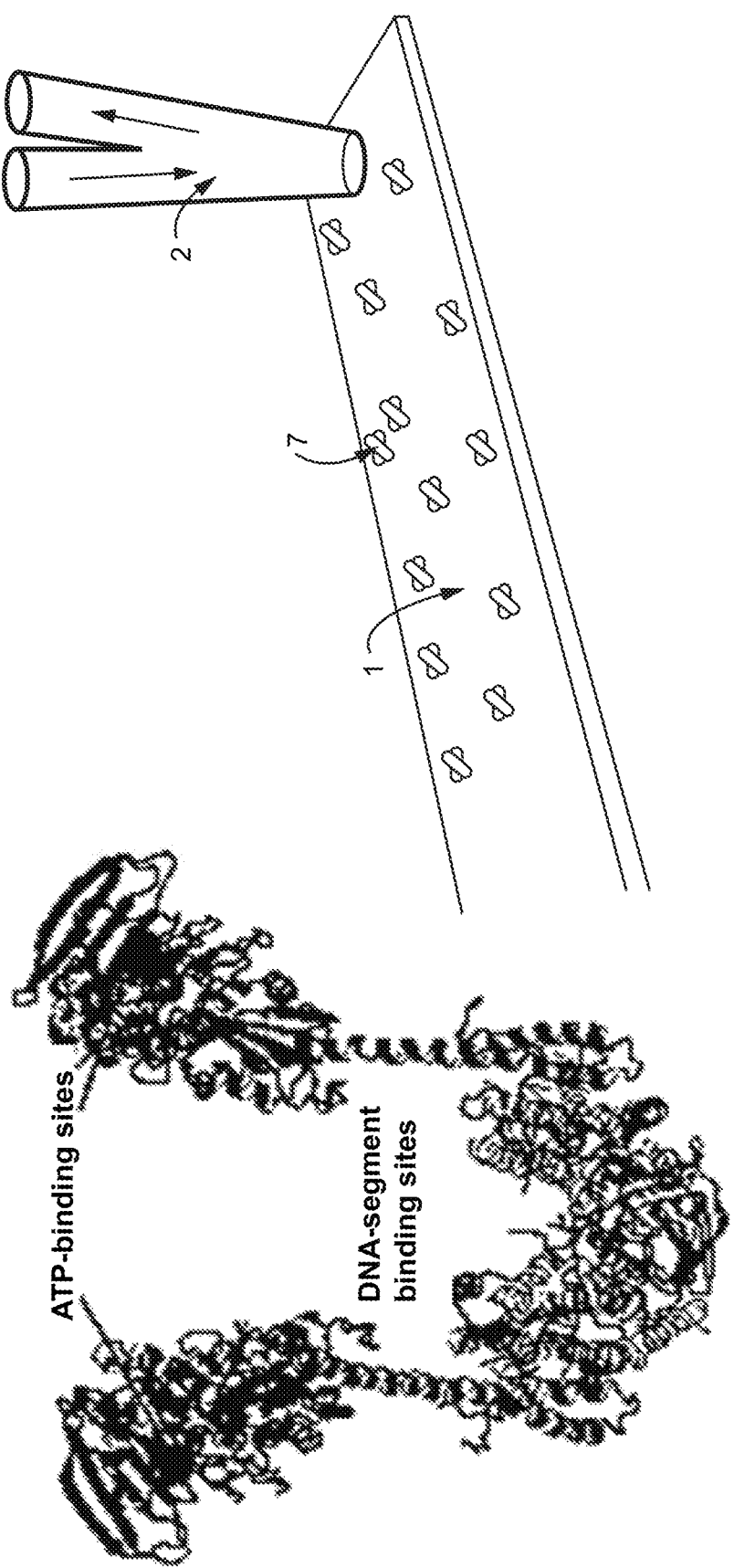
FIG. 3 illustrates a theoretical molecular structure of human TopoII and a setup according to the invention for observing TopoII drug interactions.
Figure 6:
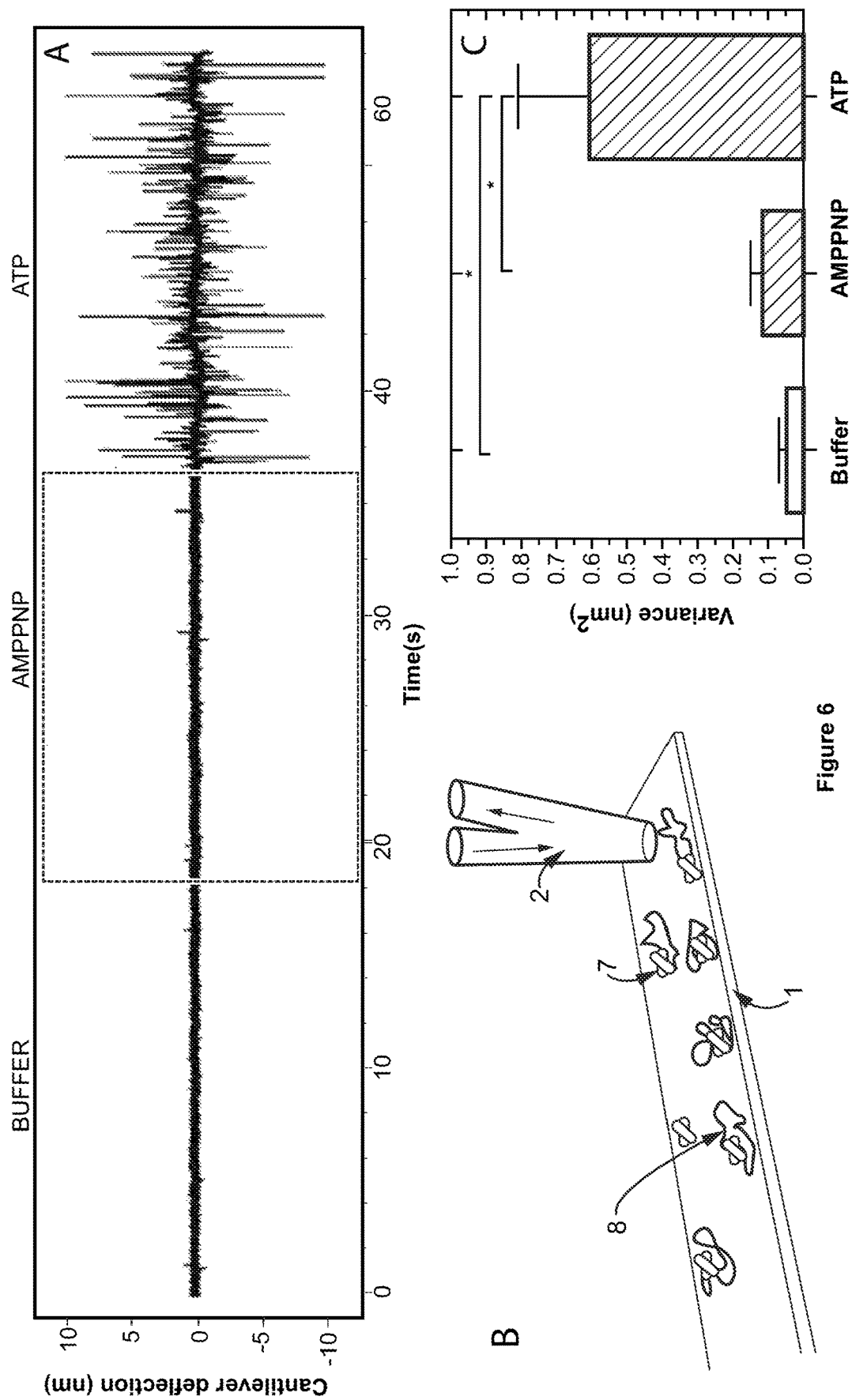
FIG. 6 represents an analysis (deflection and variance) of the interaction of human TopoII with supercoiled DNA.
Figure 7:
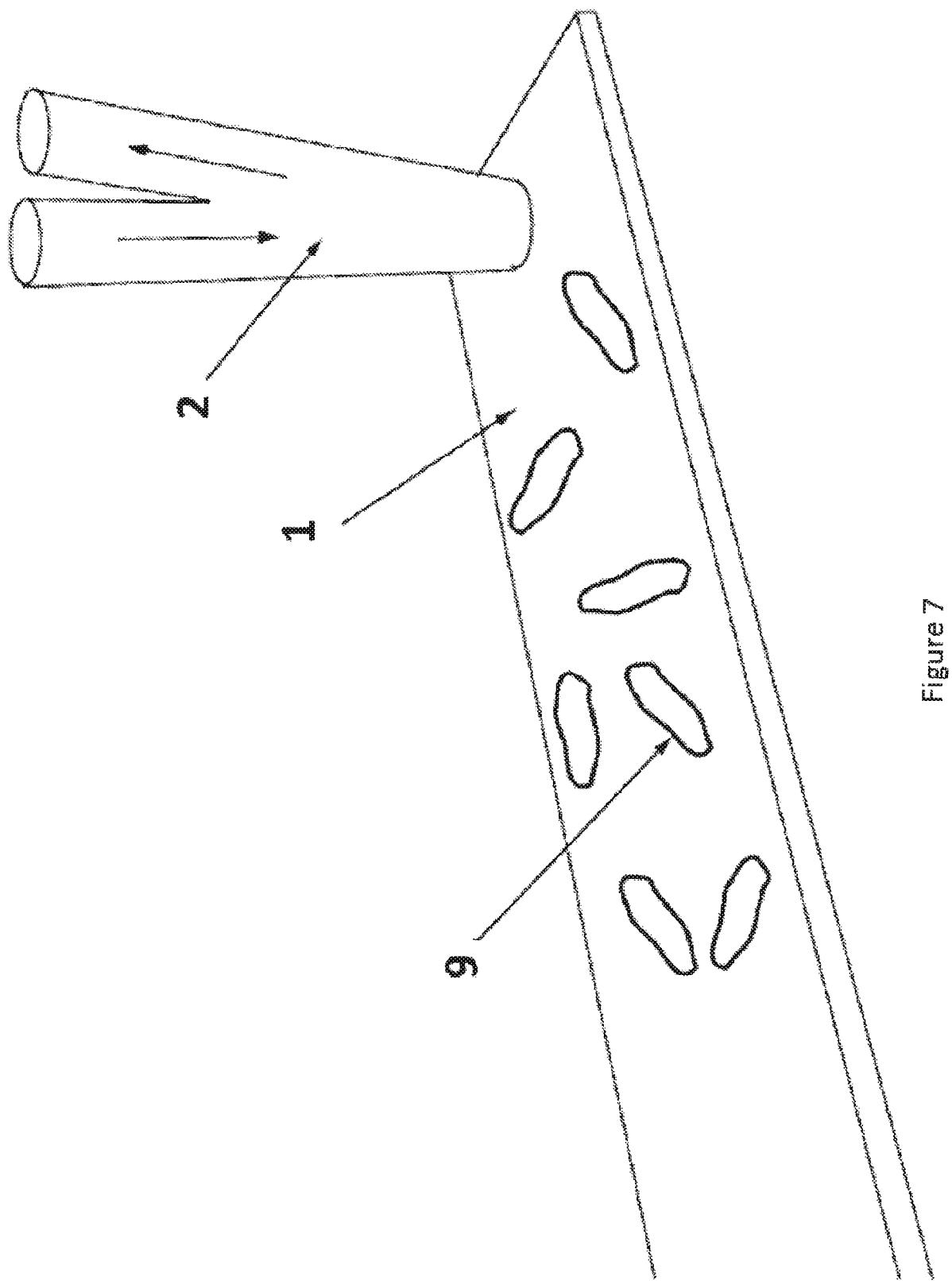
FIG. 7 illustrates another setup according to invention for observing bacteria viability following exposure to chemical and/or physical stimuli.

One or several movable objects (6-9)—see also FIGS. 3,6 and 7—to be investigated are positioned on a microsized flexible support 1,5. The fluctuations of the support 1 are recorded as a function of time. The method offers the advantage to monitor the evolution of the dynamics of the object(s), for instance as exposed to chemical or physical modifications of the environment. The system may be advantageously made of one or several fluctuating supports, an analysis chamber in which the supports are introduced and a transduction system that detects and records the support movements.

The support 1,5 may be a cantilever 1, such as those used in atomic force microscopy (AFM) (see FIGS. 1, 3, 6 and 7), an optical fibre 5, a piezoelectric system (not illustrated), a membrane or any microdevice capable of fluctuating. It has to be optimized to allow the attachment of the object on its surface by any means, for instance using chemical, biological or physical methods.

The objects 6-9 can range from single molecules to complex specimens such as nanodevices, proteins, DNA, viruses, bacteria, single cells or complex multicellular systems.

The analysis chamber preferably comprises a single or multiple inlets, a space containing the sensor and the object and one or several outlets, in order to permit exposure of the object(s) to different environmental conditions.

The transduction system, e.g. the photodetector 4, detects the fluctuations of the objects 6-9 through the support 1,5 fluctuations. It can be based on, but not limited to, optical reflection, optical interference, piezo electric, electric, magnetic, capacitive or tunneling detection systems. As examples similar systems are typically employed in AFM microscopy, microbalances or accelerometers.

The data collected by the transduction system may be advantageously analysed by a dedicated electronics optimized to highlight the dynamical component of the signal, by performing any kind of manipulation capable to evidence the variation in the object dynamics.

In a preferred embodiment, the fluctuating detector is first processed in a way to promote the attachment of the objects 6-9. In a second step the support 1,5 is exposed to the objects 6-9. This procedure can be carried on in or outside an analysis chamber. In the next step, different working conditions are produced in the analysis chamber by modifying the chemical or physical environment around the specimen. The conformational changes of the specimen or its motions, during all the described steps, induce fluctuations that are translated in measurable (electric) signals by the sensor and are recorded by the dedicated electronics. The data are finally analysed by dedicated algorithms to highlight the insurgence or modification of the specimen's movements.

Example 1

Drug Affinity Detection

These experiments involve Topoisomerase II (TopoII—FIG. 3) and its interaction with anticancerous drugs. TopoII is an essential enzyme that interacts with DNA to simplify its topology and permits the transcription to occur safely.

This enzyme requires ATP to modify its 3D conformation and to act on DNA. TopoII is also the preferred target of numerous anticancerous drugs such as aclarubicin. This drug binds to TopoII, freezes its conformation and inhibits its action (15). In the first experiment, TopoII was adsorbed onto both sides of a cantilever. It was than introduced in the analysis chamber of an AFM and its laser beam was collimated on the apex of the cantilever. The reflection of the laser beam, sent to a split photo-detector, allowed detecting the fluctuations of the cantilever as depicted in FIG. 1 and, more in detail, FIG. 3, The experiment consisted in injecting successively an ATP depleted buffer, an ATP enriched solution and an aclarubicin+ATP rich media in the analysis chamber and by recording the resulting fluctuations of the cantilever.

Figure 4:
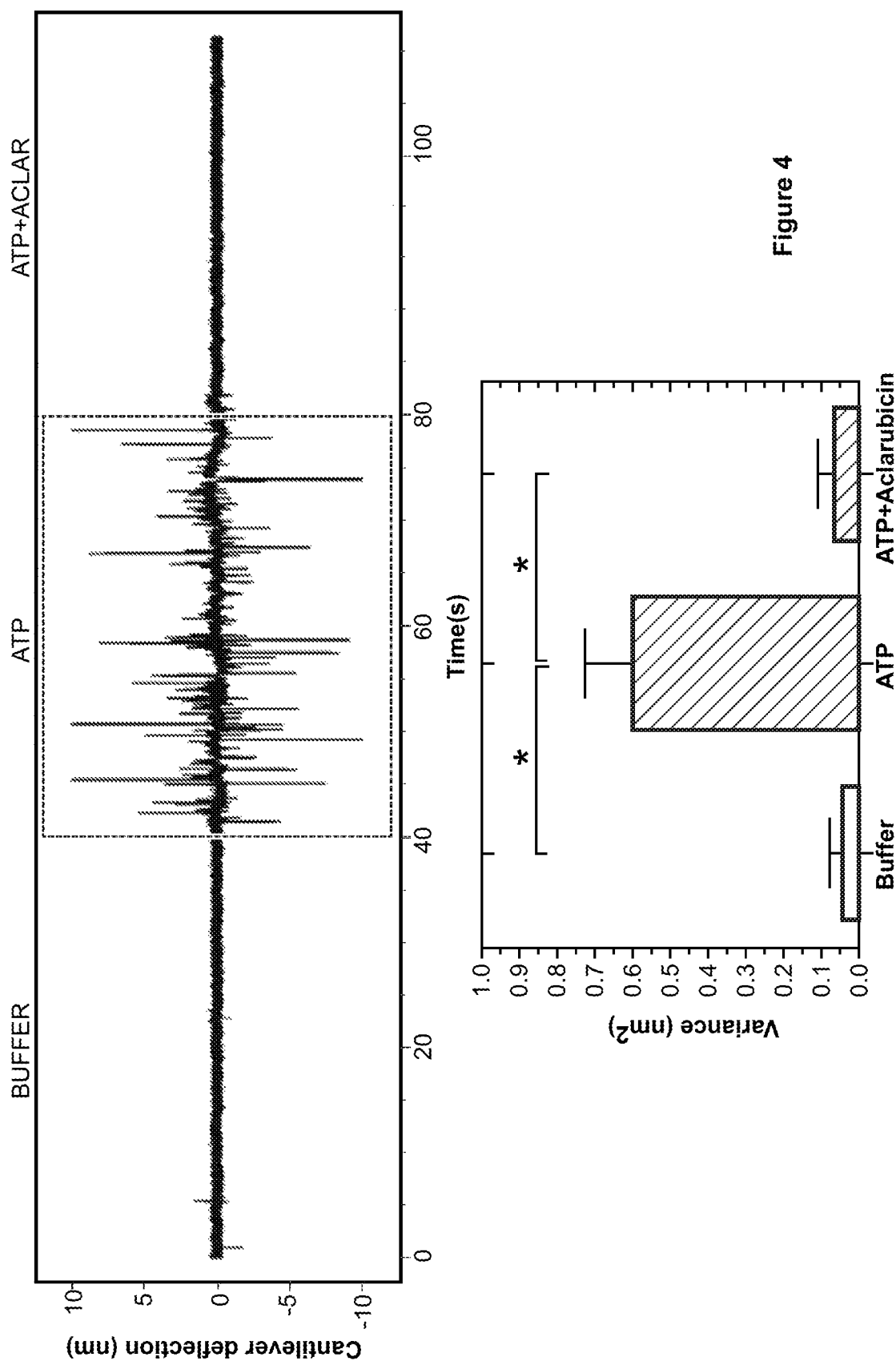
FIG. 4 represents an analysis (deflection and variance) of the interaction of human Topoisomerase II with ATP and aclarubicin (ACLAR).

By exchanging the liquid medium in which the cantilever and TopoII were immersed the inventors surprisingly noticed that the variance of the cantilever fluctuations was significantly higher in the presence of ATP compared to ATP depleted buffer or in the presence of aclarubicin, as can be seen in FIG. 4. Similar observations can also be seen with other statistical tools, other than variance calculation, like power spectrum analysis, correlation functions, wavelets, Fourier and Fast Fourier Transforms (FFT).

This experiment was performed using an APTES-coated AFM cantilever. The different buffers injected during experiment are: buffer (50 mM Tris-HCl (pH 8.0), 150 mM NaCl, 10 mM $MgCl_2$, and 0.5 mM dithiothreitol), 0.02 mM ATP and 0.02 mM ATP plus 100 µM aclarubicin. The top panel shows the cantilever deflection data, while the bottom evidences the differences of the cantilever fluctuation in terms of variance.

Figure 5:
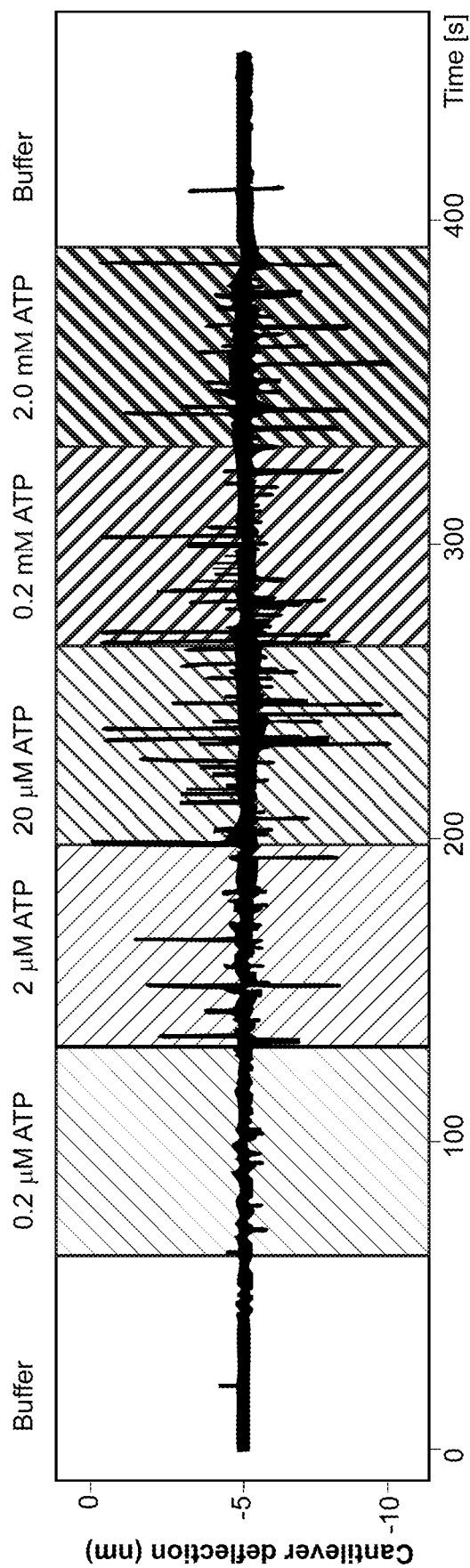
FIG. 5 represents an analysis (deflection and variance) of the interaction of human Topoisomerase II with different concentrations of ATP.
Figure 5:
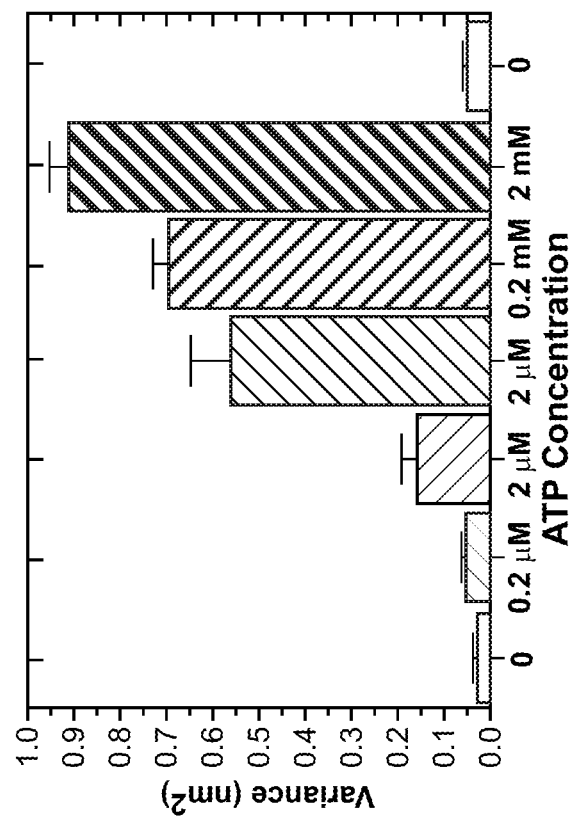

This indicates that, in the absence of ATP, TopoII was in equilibrium condition, while it was undergoing conformational changes in presence of ATP and was again in equilibrium when exposed to the action of aclarubicin. Remarkably, the conformational changes induced on the TopoII molecules by ATP were dependent on its concentration, as shown in FIG. 5. The media used in this experiment are: buffer (50 mM Tris-HCl (pH 8.0), 150 mM NaCl, 10 mM $MgCl_2$ and 0.5 mM dithiothreitol.), 0.02 mM ATP, 0.2 mM ATP, 2 mM ATP and again buffer. The top panel shows the cantilever deflection data, while the bottom one evidences the differences of the cantilever fluctuation in terms of variance.

This latter figure indicates that the proposed technique is capable of quantitatively delivering information on the conformational changes of molecules.

Example 2

Detection of Biochemical Reactions

As mentioned previously, TopoII interacts with DNA to simplify its topology. To record this reaction with our method we deposited TopoII-supercoiled DNA complexes on both sides of an AFM cantilever, as depicted in FIG. 6.

The experiment was performed using an APTES-coated AFM cantilever. The different media injected during experiment are: buffer (50 mM Tris-HCl (pH 8.0), 150 mM NaCl, 10 mM $MgCl_2$ and 0.5 mM dithiothreitol), 0.02 mM. AMPPNP (an ATP analogue) and 0.02 mM ATP. Panel A shows the cantilever deflection data. Panel B depicts the experimental set-up to follow TopoII-DNA interactions. a) DNA molecule, b) TopoII, c) AFM cantilever, d) laser beam. Panel C evidences the differences in terms of the variance.

Here again the cantilever covered with TopoII-supercoiled DNA complexes was inserted in the analysis chamber and exposed to several consecutive liquid environments: 1) ATP free solution, 2) buffer containing a non functional ATP substitute, referred to as AMPPMP 3) ATP enriched medium. AMPPMP is a non-hydrolysable ATP analogue which inhibits TopoII activity. By injecting the ATP containing solution into the analysis chamber a significant increase was noticed in the cantilever fluctuation variance as compared to the recordings done in ATP free buffers or in AMPPMP containing solutions. The results of these experiments are shown in FIG. 7.

Example 3

Antibiotic Sensitivity Detection

The presented method is sensitive enough to detect external as well as internal motion of bacteria and can be used to assess the action of antibacterial agents. This experiment shows the capability to explore the sensibility of bacteria to antibiotics with a very high temporal resolution ranging between seconds and minutes. Optionally, in the step of analyzing, a resonance frequency of the flexible support may not be taken into account.

Motile bacteria (*Escherichia coli*), resistant to kanamycin but sensitive to ampicillin, were adsorbed to both sides of a cantilever. The bacteria were successively exposed to both antibiotics to determine the impact on the bacterial motion/viability (see FIG. 7).

In these experiments the cantilever was introduced in the analysis chamber and exposed to a solution containing bacteria that eventually attached to its surface. The system was then exposed to: 1) nutriment depleted buffer, 2) nutriment solution (Lysogeny broth (LB)), 3) kanamycin-enriched LB solution 4) LB solution 5) ampicillins-enriched LB solution and, finally, 6) LB solution. It appeared that the bacterial motion increased during step 2), diminished when exposed to kanamycin at step 3), increased again in the presence of nutriment at step 4) dramatically decreased in the presence of ampicillin at step 5) and remained at the same value despite the presence of the nutrient solution at step 6).

Figure 8:
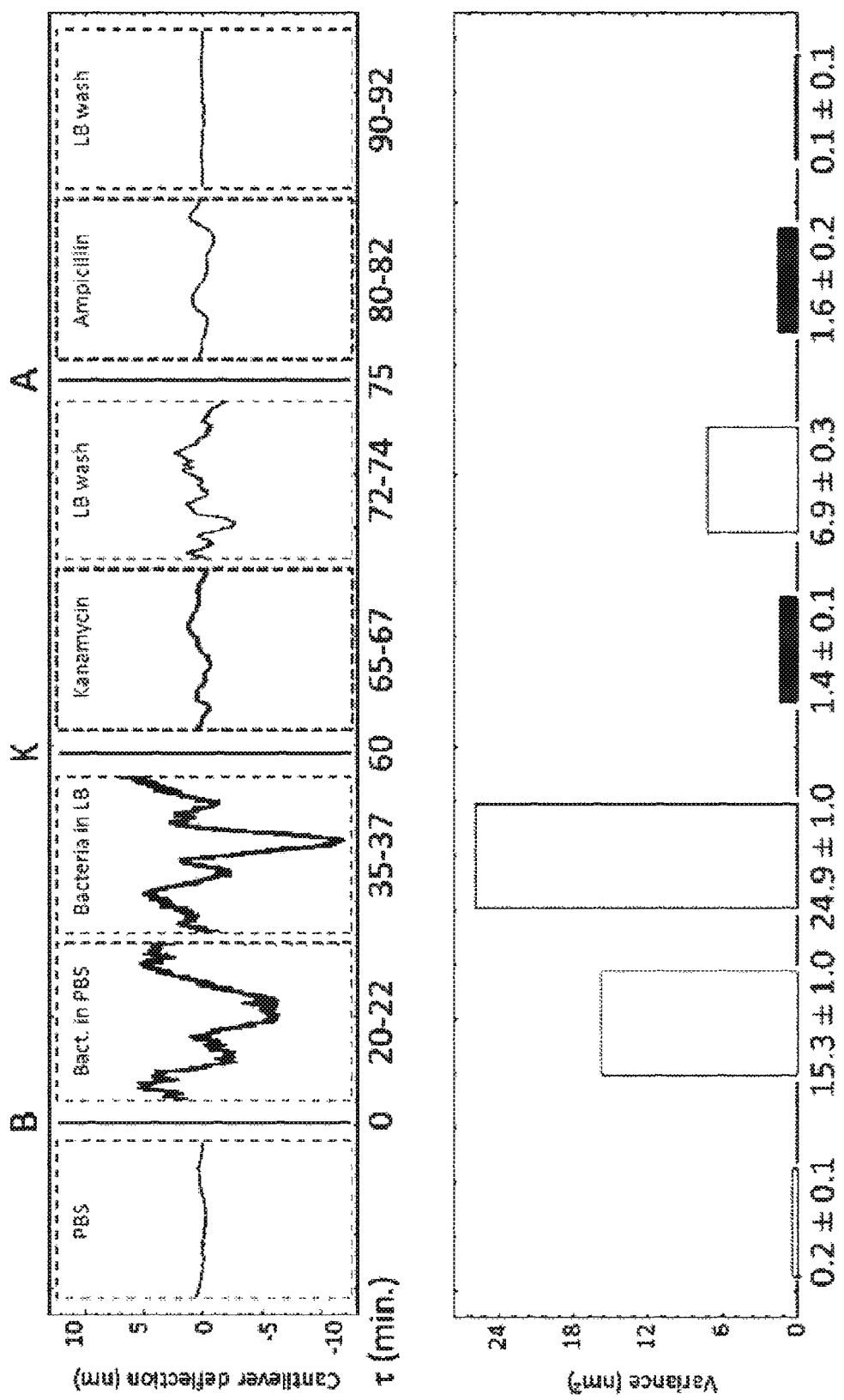
FIG. 8 represents an analysis (deflection and variance) of the resistance of E. coli to antibiotics.

FIG. 8 depicts the evolution of the cantilever fluctuations and of its STD during the different phases of the experiment, The experiment was performed using an APTES-coated AFM cantilever. The different phases of the experiment are depicted: PBS, bacteria in PBS, bacteria in LB, exposure to kanamycin, washing with LB, exposure to ampicillin, washing with LB. The top panel shows the cantilever deflection data, while the bottom one evidences the differences in terms of the variance.

Figure 9:
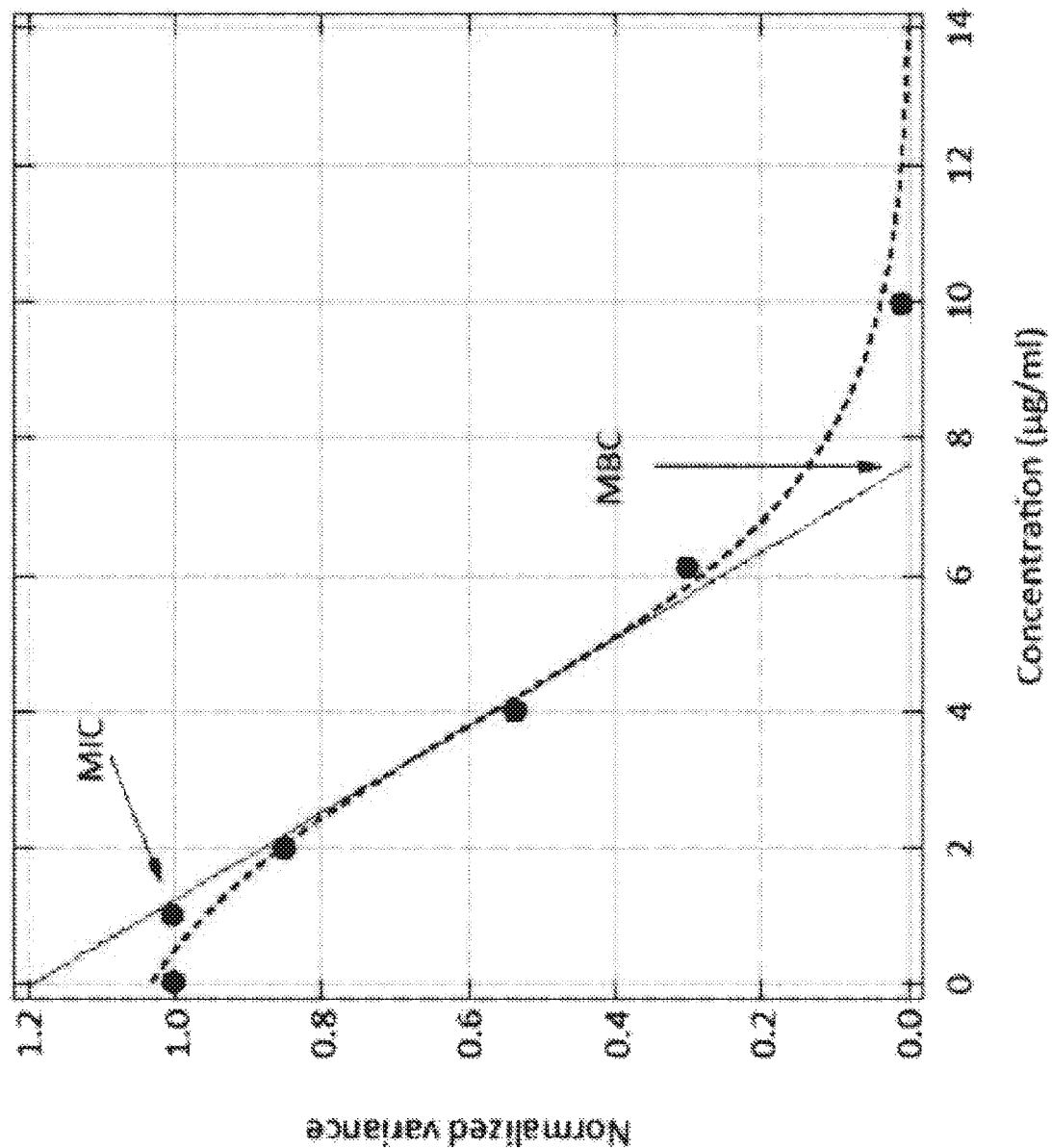
FIG. 9 represents a dose dependent analysis (variance values) with a detector according to the invention.

Similar experiments were performed, using only ampicillin as antibiotic. In particular, in a series of parallel experiments, the ampicillin concentration was changed. This allowed obtaining a quantitative dose dependence graph of the variation of the fluctuations as function of the antibiotic concentration (FIG. 9) that has been used to predict with very high accuracy the Minimum Inhibitory Concentration (MIC) and the Minimum Bactericidal Concentration (MBC). The set of experiments were performed using AFM cantilevers. The different concentrations of ampicillin cause different variance values of the cantilever's fluctuations. The curve indicates a sigmoid fit of the experimental data. The line is the tangent at the half-height variance value. The intercepts of this line with the 1.0 and 0.0 axes can be defined respectively as the MIC and MBC of the bacteria.

Figure 10:
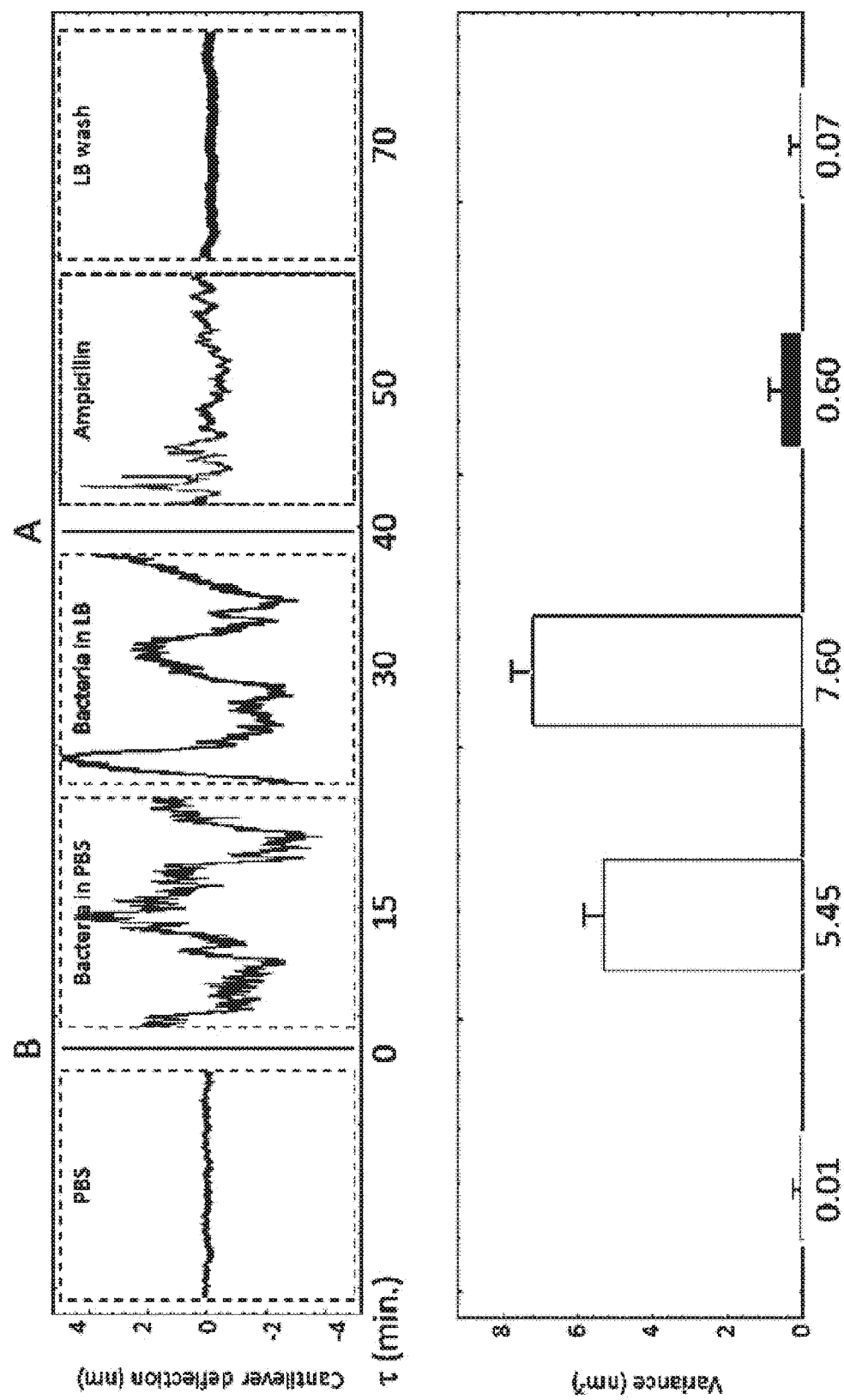
FIG. 10 represents an analysis (deflection and variance) of the exposure of Staphylococcus aureus bacteria to ampicillin.

Later on, similar experiments were repeated using non-motile bacteria (*Staphylococcus aureus*) susceptible to ampicillin. These bacteria also decreased dramatically their internal movements as soon as exposed to ampicillin. The results of the cantilever motion RMS are depicted in FIG. 10.

In this experiment an APTES-coated AFM cantilever was used. The different phases of the experiment are depicted: PBS, bacteria in PBS, bacteria in LB and exposure to ampicillin. The top panel shows the cantilever deflection data, while the bottom one evidences the differences in terms of the variance.

They demonstrate that the method can indifferently be applied to monitor motile as well as non-motile bacteria.

Finally, more experiments have been successfully carried out using, as test objects, slow growing bacteria such as *Bacillus* Calmette-Guérin (BCG, a vaccine towards the bovine tuberculosis).

To summarize, the present invention provides a device and a method that detect motion of nano to micrometer sized systems with a high spatial and temporal resolution. The method can be used to (but is not limited to) monitoring conformational changes of single molecules, biochemical reactions, drug-target interactions as well as internal and external motions of cells and bacteria. Due to its high sensitivity to movement, it can be used as a detector of life presence in extreme environments (e.g. extra-terrestrial environments). The procedure improves the existing technology (16-24) by evidencing easily and quantitatively even the slightest fluctuation of the motion detector and can be utilized in any kind of environment, especially in physiological medium. The achievable fluctuation and temporal resolution permits to predict its potential application to a vast number of fields, such as (but not limited to) cellular and molecular biology, bacteriology, microbiology, drug development, high-speed pharmaceutical evaluation, or molecule conformational monitoring. In this framework, it is of the highest interest the application of this technique to slow growing bacteria, such as *Mycobacterium tuberculosis*. Moreover, since the operating principle is extremely simple and the required materials are standard and completely reusable (electronics, microfluidics, mechanics), a device based on such invention has very low manufacturing and maintenance costs. Finally it can be easily parallelized by combining several sensors in order to improve measurement throughput and reliability.

PRIOR ART REFERENCES

1 Boisen et al., Rep. Prog. Phys., 74 (2011) 036101
2 Ilic et al., Appl. Phys. Lett., 77 (2000) 450-452
3 Braun et al., Nature Nanotech., 4 (2009)179-185
4 Lui et al., Sensors 2008 IEEE, 1464-1467
5 U.S. Pat. No. 7,148,017B1
6 Patent application US 2009235746A1
7 Patent application WO 2011021.984A1
8 Fritz et al., Science, 288 (2000) 316-318
9 Berger et al., Science, 276 (1997) 2021-2024
10 Godin et al., Nanotech., 21 (2010) 075501
11 Patent EP 1342789A2
12 Patent WO 0058729A2
13 Patent WO 03023363A2
14 Luckulum et al., Anal. Bioanal. Chem., 384 (2006) 667-682
15 Jensen et al., Cancer Res., 51 (1991): 5093-5099
16 Mckendry et al., PNAS, 99 (2002) 9783-9788
17 Gupta et al., J, Vac. Sci, Technol. B, 22 (2004) 2785-2791
18 Campbell et al. J. Bios. Bioel., 21 (2005) 462-473
19 Djuric et al., J. Microel, Eng., 84 (2007) 1639-1642
20 Patent application US 2006121502A1
21 Patent application US 2003045019A1
22 Patent application WO 2004038762A2
23 Patent application WO 03081204A2
24 Patent application US 2008.136291A1

The invention claimed is:
1. A method for analyzing a biological object with a motion detector, the motion detector including a flexible support, a sensor for measuring fluctuations of the flexible support, and electronics for analyzing the fluctuations, the biological object consisting of bacteria or cells, in presence or absence of external or internal stimuli, the method comprising the steps of:

bringing the biological object into contact with the flexible support, the biological object imparting a nanoscopic motion, measuring the fluctuations of the flexible support with the sensor while the biological object is in contact with the flexible support, the fluctuations being caused by the nanoscopic motion imparted by the biological object;

analyzing the statistical variance of the measured fluctuations by the electronics; and determining a viability of the biological object based on the analysis of a statistical variance of the measured fluctuations.

2. The method according to claim 1, wherein the step of analyzing includes calculating a statistical variance of the fluctuations of the flexible support caused by the nanoscopic motion of the biological object.

3. The method according to claim 2, wherein in the step of analyzing, an increased statistical variance of the fluctuations indicates that the fluctuations are induced by the biological object held on the flexible support.

4. The method according to claim 1, further comprising the step of: treating the biological object for facilitating an adherence of the biological object to the flexible support.

5. The method according to claim 1, wherein the biological object includes a bacteria, and the nanoscopic motion includes a motion of the bacteria.

6. The method according to claim 1, wherein the biological object is an enzyme, and the nanoscopic motion includes an interaction of the enzyme with a drug.

7. The method according to claim 1, wherein the nanoscopic motion of the biological object is intrinsic to the biological object.

8. The method according to claim 1, wherein in the step of analyzing, a resonance frequency of the flexible support is not taken into account.

9. The method according to claim 1, wherein the biological object is at least one of an enzyme and a virus.

10. The method according to claim 1, wherein the fluctuation is at least one of a vibration or a deflection.

11. A method for analyzing a biological object with a motion detector, the motion detector including a flexible support, a sensor for measuring fluctuations of the flexible support, and electronics for analyzing the fluctuations, the biological object consisting of bacteria or cells, in a presence or absence of external or internal stimuli, the method comprising the steps of:

bringing a biological object into contact with the flexible support, the biological object imparting a nanoscopic motion, measuring the fluctuations of the flexible support with the sensor while the biological object is in contact with the flexible support, the fluctuations caused by the nanoscopic motion imparted by the biological object;

analyzing the measured fluctuations by the electronics;

wherein the step of analyzing includes calculating a statistical variance of the fluctuations of the flexible support caused by the nanoscopic motion of the biological object in order to differentiate a motion of said flexible support from the motion induced by said object; and determining at least one of a presence and a modification of the nanoscopic motion of the biological object based on the analysis of the statistical variance.

12. The method according to claim 11, wherein the fluctuation is at least one of a vibration or a deflection.

* * * * *